United States Patent [19]
Waddell et al.

[11] Patent Number: 5,514,493
[45] Date of Patent: May 7, 1996

[54] PERFLUOROALKYLSULFONATES, SULFONIMIDES, AND SULFONYL METHIDES, AND ELECTROLYTES CONTAINING THEM

[75] Inventors: Jennifer E. Waddell, Burnsville; William M. Lamanna; Larry J. Krause, both of Stillwater; George G. I. Moore, Afton; Steven J. Hamrock, St. Paul, all of Minn.

[73] Assignee: Minnesota Mining and Manufacturing Company, Saint Paul, Minn.

[21] Appl. No.: 398,859

[22] Filed: Mar. 6, 1995

[51] Int. Cl.$^6$ .............................. H01M 6/04; H01M 6/16
[52] U.S. Cl. .................. 429/199; 429/198; 429/200; 429/203; 429/205; 429/192; 429/194; 252/62.2; 252/500
[58] Field of Search .................... 429/199, 198, 429/200, 203, 205, 192, 194; 252/62.2, 500

[56] References Cited

U.S. PATENT DOCUMENTS

| | | | |
|---|---|---|---|
| 2,519,983 | 8/1950 | Simons | 204/62 |
| 3,476,753 | 11/1969 | Hansen | 260/247.1 |
| 3,776,960 | 12/1973 | Koshar et al. | 260/607 A |
| 4,074,028 | 2/1978 | Will | 429/196 |
| 4,209,367 | 6/1980 | Seko et al. | 204/98 |
| 4,303,748 | 12/1981 | Armand et al. | 429/199 |
| 4,387,222 | 6/1983 | Koshar | 544/4 |
| 4,505,997 | 3/1985 | Armand et al. | 429/192 |
| 4,828,738 | 5/1989 | Tsuchiya et al. | 252/62.2 |
| 4,851,307 | 7/1989 | Armand et al. | 429/192 |
| 5,021,308 | 6/1991 | Armand et al. | 429/194 |
| 5,072,040 | 12/1991 | Armand | 564/82 |
| 5,256,821 | 10/1993 | Armand | 564/82 |
| 5,260,145 | 11/1993 | Armand et al. | 429/192 |
| 5,273,840 | 12/1993 | Dominey | 429/192 |
| 5,352,547 | 10/1994 | Kita et al. | 429/198 |

FOREIGN PATENT DOCUMENTS

| | | |
|---|---|---|
| 2096816 | 11/1993 | Canada . |
| 2239817 | 2/1974 | Germany . |
| WO93/16988 | 9/1993 | WIPO . |

OTHER PUBLICATIONS

Foropoulos, J., et al. "Synthesis, Properties, and Reactions of Bis ((trifluoromethyl)sulfonyl) Imide, $(CF_3SO_2)_2 NH^1$," *Inorganic Chemistry*, vol. 23, (1984), pp. 3720–3723.

Turowsky, J. et al., "Tris((trifluoromethyl)sulfonyl) methane, $HC(SO_2CF_3)_3$," *Inorganic Chemistry*, vol. 27, (1988), pp. 2135–2137.

Singh et al., "Chemistry of Perfluoromethylsulfonyl Perfluorobutylsulfonyl Imide," *Inorganic Chemistry*, vol. 29 (1990), pp. 2982–2985.

Webber, A. "Conductivity and Viscosity of Solutions of $LiCF_3SO_3, Li(CF_3SO_3)_2N$, and Their Mixtures," *Journal of the Electrochemical Society*, vol. 138, No. 9 (1991), pp. 2586–2590.

Fluorad™ Battery Electrolyte literature from Minnesota Mining and Manufacturing Company available in 1992.

Huckicky, M., *Chemistry of Organic Fluorine Compounds*, 2d ed., pp. 73–76 (1992).

Des Marteau, et al., "Superacids of Nitrogen and Carbon," *Journal of Fluorine Chemistry*, vol. 45, (1989), p. 24.

Krutak, J. J., et al., "Chemistry of Ethenesulfonyl Fluoirde, Fluorosulfonylethylation of Organic Compounds," *Journal Organic Chemistry*, vol. 44, No. 22, (1979) pp. 3847–3858.

*Primary Examiner*—Bruce F. Bell
*Attorney, Agent, or Firm*—Douglas B. Little; Gary L. Griswold; Walter N. Kirn

[57] ABSTRACT

An electrolyte composition that includes a salt disposed in a matrix in which the salt has a formula selected from the group consisting of

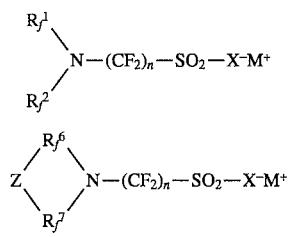

in which $X^-$ is $-O^-$, $-N^-SO_2R_f^3$, or

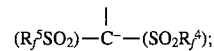

$(R_f^5SO_2)-C^- -(SO_2R_f^4);$ Z is $-CF_2-$, $-O-$, $-NR_f^8-$, or $-SF_4-$; $R_f^1$ and $R_f^2$, independently, are $-CF_3$, $-C_mF_{2m+1}$, or $-(CF_2)_q-SO_2-X^-M^+$; $R_f^3$, $R_f^4$, and $R_f^5$, independently, are $-CF_3$, $-C_{mf2m+1}$, $-(CF_2)_q-X^-M^+$,

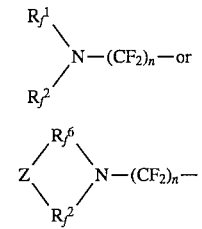

$R_f^8$ is $-CF_3$, $-C_mF_{2m+1}$, or $-(CF_2)_q-SO_2-X^-M^+$; $R_f^6$ and $R_f^7$, independently, are perfluoroalkylene moieties having the formula $-C_rF_{2r}$; n is 1–4; r is 1–4; m is 1–12; q is 1–4; and $M^+$ is a counterion.

14 Claims, No Drawings

PERFLUOROALKYLSULFONATES, SULFONIMIDES, AND SULFONYL METHIDES, AND ELECTROLYTES CONTAINING THEM

BACKGROUND

This invention relates to fluorinated electrolyte salts useful in battery electrolyte compositions.

Electrolyte salts for use in electrochemical cells, e.g., lithium or lithium ion cells, must exhibit good ionic conductivity, electrochemical stability, thermal stability, and chemical stability. In addition, the components of the electrochemical cell must be stable towards the electrolyte. Stability concerns are particularly acute in the case of electrochemical cells having aluminum cathode current collectors because the aluminum is susceptible to corrosion.

Among the known electrolyte salts, lithium bis(trifluoromethanesulfonyl)imide (($CF_3SO_2)_2N^-Li^+$) has excellent conductivity and stability, but is highly corrosive. $LiPF_6$ has excellent conductivity and is not corrosive, but is thermally and hydrolytically unstable. $LiO_3SCF_3$ (also called lithium triflate) has good thermal and chemical stability, but has low conductivity and is highly corrosive.

Indeed, the corrosion of aluminum in electrolytes containing lithium triflate or lithium bis(trifluoromethanesulfonyl)imide is so severe as to make these salts of little use for applications in the more advanced, high voltage cells. Thus, the use of presently-available electrolyte salts in high voltage lithium or lithium-ion cells has resulted in batteries having suboptimal performance characteristics such as restricted operating temperature ranges and limited discharge/charge rates and inadequate cycling performance, particularly when aluminum components are used.

DISCLOSURE OF INVENTION

The present invention provides salts of fluorochemical anions that are highly conductive in nonaqueous, polar organic media and inhibit corrosion of aluminum at high oxidation potentials and are therefore useful as electrolytes in high voltage electrochemical cells, such as lithium batteries, which contain aluminum components. The fluorochemical salts are comprised of a cationic portion which is a metal cation and an anionic portion. The invention further provides electrochemical cells or batteries containing such electrolyte salts and aluminum components.

The particular cation chosen as the cationic portion of the salt is normally dictated by the type of electrochemical cell in which the electrolyte will be used and the attendant cell chemistry. Classes of metal cations useful as the cationic portion of the salts of this invention include: $Li^+$, $Na^+$, $K^+$, $Ca^{++}$, $Mg^{++}$, $Zn^+$, or $Al^{+++}$. Of these $Li^+$, $Na^+$, $K^+$, $Ca^{++}$, $Mg^{++}$ are preferred with $Li^+$ being most preferred.

In one aspect, the invention features an electrolyte composition that includes a salt disposed in a matrix in which the salt has a formula selected from the group consisting of

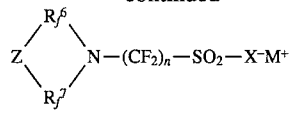  (1)

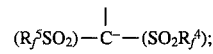 (2)

in which $X^-$ is $—O^-$, $—N^-SO_2R_f^3$, or

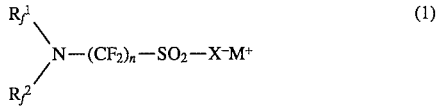

Z is $—CF_2—$, $—O—$, $—NR_f^8—$, or $—SF_4—$; $R_f^1$ and $R_f^2$, independently, are $—CF_3$, $—C_mF_{2m+1}$, or $—(CF_2)_q—SO_2—X^-M^+$; $R_f^3$, $R_f^4$, and $R_f^5$, independently, are $—CF_3$, $—C_mF_{2m+1}$, $—(CF_2)_q—SO_2—X^-M^+$,

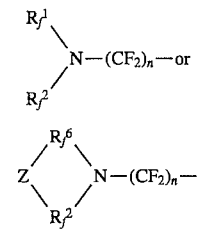

$R_f^8$ is $—CF_3$, $—C_mF_{2m+1}$, or $—(CF_2)_q—SO_2—X^-M^+$; $R_f^6$ and $R_f^7$, independently, are perfluoroalkylene moieties having the formula $—C_rF_{2r}$; n is 1–4; r is 1–4; m is 1–12 preferably 1–8; q is 1–4; and $M^+$ is a counterion.

$M^+$ is preferably selected from the group consisting of alkali metals, alkaline earth metals, transition metals, rare earths, and nitrogen onium ions, e.g., ammonium, alkyl ammonium, or guanidinium ions such as $NH_{(4-j)}R_j^+$, $R_jC(NH_{(2-j)}R_j)_2^+$, or $C(NH_{(2-j)}R_j)^+_3$ in which j is 0–2 and $R_j$ is $—H$, an alkyl group (e.g., having between 1 and 5 carbon atoms, inclusive), an oxalkyl group (e.g., having between 1 and 5 carbon atoms, inclusive), or an aryl group (e.g., phenyl), with lithium counterions being particularly preferred. $M^+$ may be $H^+$.

Preferred salts include sulfonates ($X^-$ is $—O^-$), imides ($X^-$ is $—N^-SO_2R_f^3$), and methides

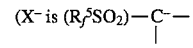

($SO_2R_f^4$). Examples of particularly preferred salts include salts having the following formulae:

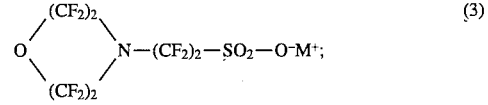 (3)

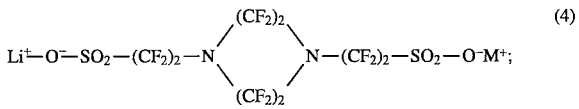 (4)

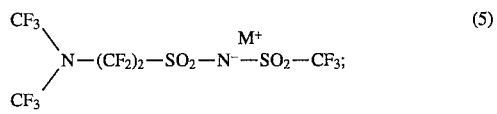 (5)

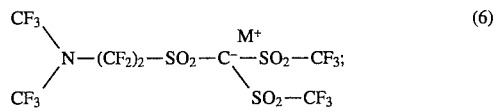 (6)

-continued

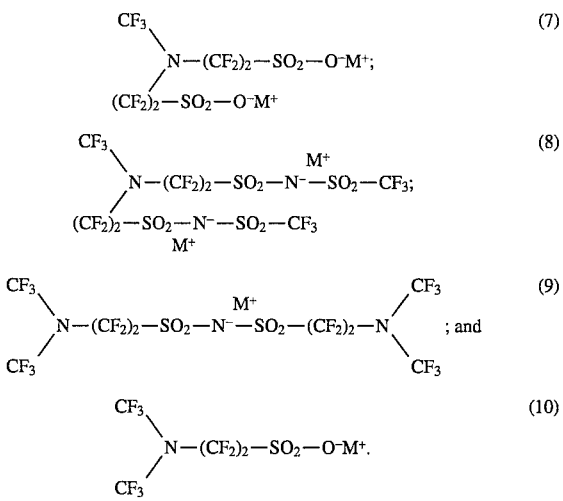

The electrolyte composition may further include another salt selected from the group consisting of $M^+BF_4^-$; $M^+SbF_6^-$; $M^+AsF_6^-$; $M^+ClO_4^-$; $M^+C^-(SO_2CF_3)_3$; $M^+PF_6^-$; $CF_3SO_3^- M^+$; $(CF_3SO_2)_2N^-M^+$; and combinations thereof, where $M^+$ is a counterion.

Examples of preferred matrix materials include solid matrices (e.g., macromolecular materials), aprotic liquid media, and mixtures thereof.

The invention further features an electrochemical cell that includes an anode, a cathode (e.g., comprising an aluminum current collector), and the above-described electrolyte compositions. Examples of preferred electrochemical cells include primary and secondary lithium batteries.

In another aspect, the invention features a salt having a formula selected from the group consisting of

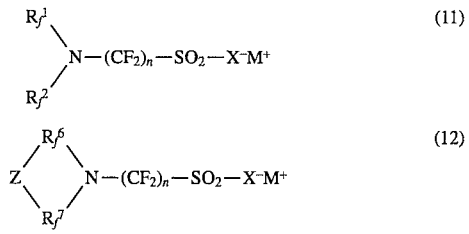

in which $X^-$ is $-N^-SO_2R_f^3$ or $(Rf_2SO_2)-C^--(SO_2R_f^4)$; Z is $-CF_2-$, $-O-$, $-NR_f^8-$, or $-SF_4-$; $R_f^1$ and $R_f^2$, independently, are $-CF_3$, $-C_mF_{2m+1}$, or $-(CF_2)_q-SO_2-$ $Q^-M^+$; Q is $-O^-$, $-N^-SO_2R_f^3$ or $(Rf_2SO_2)-C^--(SO_2R_f^4)$; $R_f^3$, $R_f^4$, and $R_f^5$, independently, re $-CF_3$, $-C_mF_{2m+1}$, $-(CF_2)_q-SO_2-Q^-M^+$,

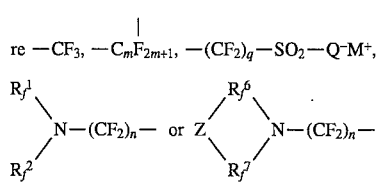

$R_f^8$ is $-CF_3$, $-C_mF_{2m+1}$, or $-(CF_2)_q-SO_2-Q^-M^+$; $R_f^6$ and $R_f^7$, independently, are perfluoroalkylene moieties having the formula $-C_rF_{2r}$; n is 1–4; r is 1–4; m is 1–12 preferably 1–8; q is 1–4; and $M^+$ is a counterion. Preferred salts include those according to formulae (5), (6), (8), and (9), above.

Throughout this application the following definitions apply:

"Matrix" refers to a medium (e.g., a solid, liquid, or gel) in which salts according to formulae (1) and (2) may be dissolved or dispersed to form an ionically conductive electrolyte composition.

"Macromolecular material" refers to a homopolymer, copolymer, or combination thereof, which may or may not be cross-linked.

"Gel" refers to a cross-linked polymer swollen with solvent.

"Battery" includes all electrical energy storage devices, including capacitors, fuel cells, electrochromic devices, and electrochemical cells.

The inventive compositions exhibit unexpected benefits in electrochemical performance. Specifically, the invention provides electrolyte compositions that exhibit high ionic conductivity and excellent electrochemical, thermal, and hydrolytic stability, yet at the same time inhibit degradation of aluminum battery components (e.g., corrosion of aluminum components such as current collectors) at voltages typically encountered during battery operation (e.g., potentials up to and including 5 V vs. Li/Li$^+$ in the case of lithium batteries). The inventive electrolytes are useful in high voltage, primary or secondary batteries having aluminum components, such as the current collector.

The inventive salts provide all of the desirable features previously associated with $Li^+ N(SO_2CF_3)_2$, such as high ionic conductivity and high electrochemical, thermal, and chemical stability. Furthermore, they avoid the use of toxic elements (such as As and Sb) which could be harmful to the environment, and they pose no known explosion hazard (as with perchlorate). Therefore, salts of this invention provide much improved properties for use in nonaqueous electrolytes for high voltage, primary or secondary, lithium or lithium-ion batteries which contain aluminum components.

DETAILED DESCRIPTION

Electrolyte compositions according to the invention include a matrix in which is disposed one or more perfluoroorganic sulfonyl salts having the structure set forth under Disclosure of Invention, above. Each of these salts contains at least one perfluoro-organic sulfonyl linkage or group in which at least one heteroatom (e.g. N, O, or S) interrupts the perfluorocarbon chain of the perfluoro-organic group. The electrolyte compositions based upon these salts are particularly useful in primary and secondary lithium batteries containing aluminum cathode current collectors because they do not promote aluminum corrosion at voltages typically encountered during battery operation (e.g., in the range 0.5 to 5.0 V vs. Li).

In general, the above-described perfluoroorganic sulfonate salts are prepared by hydrolysis of the corresponding perfluoroorganosulfonyl fluoride, via reaction with a basic salt having the desired cation (e.g., a carbonate, hydroxide, or alkoxide salts) in the presence of water and, optionally, an additional polar solvent.

Processes useful for the synthesis of fluorochemical imide salts and their conjugate acids are described in:

1. D. D. Des Marteau et al., *Inorg. Chem.*, 1984, 23 pp., 3720–3723;
2. D. D. Des Marteau et al., *Inorg. Chem.*, 1990, 29 pp., 2982–2985;
3. Canadian Patent 2000142-A;
4. U.S. Pat. No. 4,505,997; and
5. U.S. Pat. No. 5,072,040.

Processes useful for the synthesis of fluorochemical methide salts and their conjugate acids are described in:

1. U.S. Pat. No. 5,273,840; and
2. Turowsky and Seppelt, *Inorg. Chem.*, (1988) 27 pp., 2135–2137.

To prepare the perfluoroorganosulfonyl fluoride, the corresponding hydrocarbon sulfonyl fluoride (prepared, e.g., according to techniques described in Hansen, U.S. Pat. No. 3,476,753; which is incorporated by reference) is perfluorinated by electrochemical fluorination according to the methods described in Hansen U.S. Pat. No. 3,476,753, Simons, U.S. Pat. No. 2,519,983 and *Chemistry of Organic Fluorine Compounds*, Milos Hudlicky, ed., 2d ed., PTR Prentice Hall (New York), pp. 73–76, (all of which are incorporated by reference), followed by purification.

To form the electrolyte composition, the salt is mixed with the matrix material such that the salt is at least partially dissolved or dispersed in the matrix material. The salt is preferably employed at a concentration such that the conductivity of the electrolyte solution is at or near its maximum value, although a wide range of other concentrations will also serve.

The matrix material may be in the form of a solid, liquid, gel or a liquid impregnated porous membrane. For battery applications, the matrix is chosen to provide the particular conductance, viscosity, mechanical strength, and reactivity properties desired for the electrolyte.

Preferred metal cations and preferred solvents or matrix materials are dependent on cathode and anode construction in the battery. For lithium batteries (having a lithium anode) the preferred cation is $Li^+$, and the preferred solvents are aprotic (e.g., excluding water and alcohols).

Mixtures of matrix materials can be employed and are sometimes preferred in tailoring the matrix material's properties to provide optimum performance. In general, the amount of matrix material is selected such that the salt concentration ranges from about 0.75M to about 2.5M.

Suitable solvents for preparing electrolyte solutions can be liquid, polymeric or mixtures of polymer and liquid. Examples of suitable solid matrix materials include polymers and copolymers such as poly(ethylene oxide), polyesters, polyacrylates, polyphosphazenes, polysiloxanes, poly (propylene oxide), fluoropolymers (e.g., poly (vinylidene fluoride)), and poly (acrylonitrile), as well as the polymers and copolymers described in Armand et al., U.S. Pat. No. 4,505,997, hereby incorporated by reference, and mixtures thereof. The polymers may be used in cross-linked or uncross-linked form. Such materials are generally dry, i.e., have a water content less than about 100 ppm, preferably less than about 50 ppm.

Examples of suitable liquid matrix materials include water and polar organic liquids such as ethylene glycol, methanol, ethanol, 2-ethoxy ethanol, and 2-(2-ethoxy ethoxy) ethanol. In batteries comprising a highly reducing electrode (such as lithium metal) nonaqueous polar, aprotic liquid electrolytes are preferred. Such liquids are generally dry, i.e., have a water content less than about 100 ppm, preferably less than about 50 ppm. Examples of suitable aprotic liquids include linear ethers such as diethyl ether, diethylene glycol dimethyl ether, and 1,2-dimethoxyethane; cyclic ethers such as tetrahydrofuran, 2-methyltetrahydrofuran, dioxane, dioxolane, and 4-methyldioxolane; esters such as methyl formate, ethyl formate, methyl acetate, dimethyl carbonate, diethyl carbonate, propylene carbonate, ethylene carbonate, and butyrolactones (e.g., gamma butyrolactone); nitriles such as acetonitrile and benzonitrile; nitro compounds such as nitromethane or nitrobenzene; amides such as N,N-dimethylformamide, N,N-diethylformamide, and N-methylpyrrolidinone; sulfoxides such as dimethyl sulfoxide; sulfones such as dimethylsulfone, tetramethylene sulfone, and other sulfolanes; oxazolidinones such as N-methyl-2-oxazolidinone; and mixtures thereof. Maximum conductivities of the electrolyte salts of this invention in typical nonaqueous, polar, aprotic liquid media (e.g., propylene carbonate) are generally in the range of 0.01–20 mS/cm, (milliSiemens per centimeter) at room temperature, preferably greater than 1 ms/cm.

In some cases, it may be desired to add other salts to the electrolyte composition in order to maximize performance. Such salts include, but are not limited to, alkali metal, alkaline earth metal, and Group IIIB metal (e.g., aluminum) salts of anions such as $BF_4^-$; $PF_6^-$; $AsF_6^-$; $ClO_4^-$; $SbF_6^-$; $R_fSO_3^-$ (in which Rf is a perfluoroalkyl group having between 1 and 12 carbon atoms, inclusive); a bis-(perfluoroalkylsulfonyl)imide anion $(R_f\text{---}SO_2\text{---}N^-\text{---}SO_2\text{---}R_f')$ in which $R_f$ and $R_f'$, independently, are perfluoroalkyl groups having between 1 and 12 carbon atoms, inclusive; a bis-perfluoroalkylsulfonyl methide anion $(R_{f\text{---}SO_2}\text{---}C^-(R)\text{---}SO_2\text{---}R_f')$ in which $R_f$ and $R_f'$, independently, are perfluoroalkyl groups having between 1 and 12 carbon atoms, inclusive, and R is H, Br, Cl, I, an alkyl group having between 1 and 20 carbon atoms, inclusive, aryl, or alkylaryl; and a tris-(perfluoroalkylsulfonyl)methide anion $(\text{---}C(SO_2R_f)(SO_2R_f')(SO_2R_f''))$ in which $R_f$, $R_f'$, and $R_f''$, independently, are perfluoroalkyl groups having between 1 and 12 carbon atoms, inclusive. Such salts also include cyclic perfluoroaliphatic disulfonylimide salts, such as those described in U.S. Pat. No. 4,387,222 (Koshar), and metal salts of acids, such as those described by DesMarteau et al. in *J. Fluor. Chem.* 45, 24 (1989).

Representative examples of suitable salts include $LiOH \cdot H_2O$, $LiBF_4$, $LiAsF_6$, $LiClO_4$, $LiPF_6$, $CF_3SO_3Li$, $C_2F_5SO_3Li$, $C_{10}F_{21}SO_3Li$, $(CF_3SO_2)_2NLi$, $(CF_3SO_2)_2NNa$, $[(CF_3SO_2)_2N]_3Al$, $(CF_3SO_2)_2C(H)Li$, cyclo-$(CF_2SO_2)_2NLi$, cyclo-$(CF_2SO_2)_2C(H)Li$, $(CF_3SO_2)_3CLi$, and mixtures thereof.

The material comprising the anode of an electrochemical cell is preferably lithium metal. It may be used as a pure foil, carried on aluminum foil backing or pressed into expanded metal screen and alloyed with various other metals. The lithium may also be intercalated into a host material such as carbon or inorganic host materials that are intercalatable.

The cathodes of the electrochemical cell of the invention are generally particles of an electrochemically active material bound into a plastic material such as ethylene-propylene-diene (EPDM) terpolymer, or particles of an active material mixed in a binder of carbon, emulsified Teflon PTFE, or both, which is in turn pressed into an expanded metal screen, preferably aluminum, which serves as the current collector. In polymer electrolyte batteries the polymer electrolyte can act as the active material binder.

The invention is illustrated further by the following examples.

EXAMPLES

Example 1

Synthesis of Lithium Perfluoro-(N-sulfoethyl)morpholine (formula (3))

To a 250 mL flask fitted with a condenser, addition funnel, magnetic stirrer and a heated oil bath was charged 6.09 g $LiOH(H_2O)$, and 50 mL each of water and isopropanol.

Perfluoro-(N-fluorosulfoethyl)morpholine (20.0 g) (prepared by electrochemical fluorination of N-fluorosulfoethyl morpholine which, in turn, was prepared by addition of morpholine to vinylsulfonyl fluoride as described in Krutak et al., *J. Org. Chem.*, 44(2):3847–58 (1979)) was added dropwise with stirring at 60° C. under a nitrogen atmosphere. Once addition was complete the reaction was allowed to continue with stirring for 17 hours at 60° C. After cooling to room temperature, dry ice pellets, followed by diatomaceous earth, were added to the reaction solution to form a slurry. The slurry was then filtered to give a milky white filtrate. The filtrate was evaporated to dryness at 80°–110° C. and about 40 torr, and the solid white residue was redissolved in 125 mL of warm ethanol. After cooling to room temperature, the mixture was filtered by suction through a nylon microfiltration membrane having 0.1 micrometer average pore size. The filter cake was then washed with an additional 50 mL of ethanol. Next, the ethanol was removed under reduced pressure, after which two 40 mL portions of toluene were added to the residue and subsequently evaporated at 80° C., 20 torr in order to remove the residual ethanol and water. The resulting white powder was transferred to a vacuum oven and dried further at 120° C., $10^{-2}$ torr for about 16 hours. A total of 18.7 g of a white powder was recovered corresponding to 93% yield based on sulfonyl fluoride. The structure of the product was confirmed by $^1$H and $^{19}$F NMR and FTIR to be that of the title salt.

Example 2

Synthesis of Dilithio Perfluoro(N,N'-bis-sulfoethyl)piperazine (formula (4))

To a 500 mL flask fitted with a condenser, magnetic stirrer and a heated oil bath was charged 10.59 g LiOH(H$_2$O), 30 g of perfluoro(N,N'-bis-fluorosulfoethyl)piperazine (prepared by electrochemical fluorination of N,N'-bis-fluorosulfoethyl piperazine which, in turn, was prepared by addition of piperazine to vinylsulfonyl fluoride as described in Krutak et al., *J. Org. Chem.*, 44(2):3847–58 (1979)) and 100 mL each of water and isopropanol. After stirring under a nitrogen atmosphere for 1 hour at room temperature the reaction mixture was heated to 60° C. for 25 hours. After cooling to room temperature, the reaction solution was treated with dry ice pellets and diatomaceous earth, and filtered as in Example 1. The filtrate was evaporated to dryness at 80°–110° C. and about 40 torr, and the solid white residue was redissolved in 175 mL of warm ethanol. After cooling to room temperature, the mixture was filtered by suction through a nylon microfiltration membrane having 0.1 micrometer average pore size, and the filtrate set aside. The filter cake was then washed with an additional 75 mL of ethanol, and the resulting filtrate combined with the filtrate from the nylon microfiltration membrane filtration. Next, the combined filtrates were evaporated at 30°–80° C., 20 torr, and then two 75 mL portions of toluene were added to the residue and subsequently removed by rotary-evaporation at 80° C., 20 torr in order to drive off residual ethanol and water. The resulting white powder was transferred to a vacuum oven and dried further at 120° C., 0.01 torr for about 16 hours. A total of 29.2 g of a white powder was recovered corresponding to 96% yield based on sulfonyl fluoride. The structure of the product was confirmed by $^1$H and $^{19}$F NMR and FTIR to be that of the title salt.

Example 3

Synthesis of Lithium trifluoromethylsulfonyl perfluoro(dimethylaminoethylsulfonyl)imide Li$^+$⁻N(SO$_2$CF$_3$)(SO$_2$C$_2$F$_4$N(CF$_3$)$_2$) (formula (5))

The hydrocarbon precursor 2-dimethylaminoethylsulfonylfluoride was made by the addition of dimethylamine to vinylsulfonyl fluoride as described in Krutak et al., *J. Org. Chem.*, 44(2):3847–58 (1979). The hydrocarbon was perfluorinated by electrochemical fluorination. An electrochemical cell of the type described in U.S. Pat. No. 2,519,983 (Simons) was filled with 1500 cm$^3$ HF. The cell was operated at 31 psig (214 Kpa) and at an average temperature of 56° C. During the course of the 129 hour run, 456 grams of fluorinated product was produced from 650 grams (4.2 mole) of starting material. Analysis of the fluorocarbons was done using gas chromatography/FTIR to confirm structures and yields. The resulting fluorochemical was distilled on a 3-plate column to a main cut of 374 grams (1.1 moles, 27% molar yield) corresponding to perfluorodimethylaminoethylsulfonyl fluoride ((CF$_3$)$_2$NC$_2$F$_4$SO$_2$F).

To a dry flask equipped with a reflux condenser and magnetic stirrer was charged 1.13 g CF$_3$SO$_2$NH$_2$ (prepared, e.g., as described in Foropoulos and DesMarteau, *Inorg. Chem.*, 23:3720–23 (1984)), 20 mL anhydrous triethylamine (distilled from LiAlH$_4$) and 2.67 g (CF$_3$)$_2$NC$_2$F$_4$SO$_2$F. The reaction mixture was heated to 70° C. under a nitrogen atmosphere with stirring for 17 hours, after which volatile components were removed under reduced pressure. The residue was treated with a mixture of 40 mL water and 40 mL methylene chloride with stirring to form a two phase mixture. The methylene chloride phase was then separated, washed with two 40 mL portions of fresh water to remove water-soluble components, dried over anhydrous MgSO$_4$, filtered and then evaporated under reduced pressure to yield a dark red liquid. The liquid residue was combined with 20 mL of conc. sulfuric acid in a short path distillation apparatus equipped with a dry-ice cooled condenser, and then vacuum distilled at $10^{-3}$ torr, 60° C. The distillate was dissolved in 50 mL of diethyl ether, after which the resulting ether solution was treated with excess lithium carbonate for 2 hours with stirring at room temperature, filtered and the filtrate evaporated under reduced pressure to yield a clear, colorless oil. Approximately 100 mL of toluene were combined with the oil and the mixture evaporated again at 40°–70° C., 20 torr, causing the oil to solidify to form the title salt. The structure of the product was confirmed by $^1$H and $^{16}$F NMR.

Example 4

Synthesis of Lithium bis-(trifluoromethylsulfonyl) (perfluorodimethylaminoethylsulfonyl)methide Li$^+$⁻C(SO$_2$CF$_3$)$_2$(SO$_2$C$_2$F$_4$N(CF$_3$)$_2$) (formula (6))

166.8 g of bis-trifluoromethylsulfonyl methane (CH$_2$(SO$_2$CF$_3$)$_2$), prepared as described in Koshar et al., U.S. Pat. No. 3,776,960, was dissolved in anhydrous diethyl ether (400 mL). Anhydrous NaCO$_3$ was then added to the solution and the resulting mixture stirred at room temperature under nitrogen. When CO$_2$ evolution was no longer evident, acetone (100 mL) was added and the mixture filtered, the insoluble salts washed with acetone, and the filtrate evaporated under reduced pressure to yield Na$^+$⁻CH(SO$_2$CF$_3$)$_2$ (179.9 g).

Under a nitrogen atmosphere, 15.0 g anhydrous $Na^+$ $CH(SO_2CF_3)_2$ and 80 mL anhydrous tetrahydrofuran (THF) were charged to a dry Schlenck flask equipped with a magnetic stirrer and reflux condenser. The solution was cooled to 0° C. and 37.2 ml of 1.4M methyllithium in diethyl ether added dropwise with stirring. After about 10 min, 18.3 g anhydrous $(CF_3)_2NC_2F_4SO_2F$ (degassed by bubbling nitrogen through it) was added at 0° C. with stirring. The reaction mixture was allowed to warm to room temperature where it was held for 18 hours, followed by 23 hours of heating at reflux. Upon cooling to room temperature a white solid precipitated which was removed by filtration. The filtrate was evaporated at 70° C., 20 torr to give a dark brown oil. The oil was dissolved in 100 mL water and extracted with three 100 mL portions of methylene chloride. The brown aqueous phase was then treated with 25 g $Cs_2CO_3$ in 150 mL water, causing precipitation of a dark-brown, gummy material. The mixture was triturated at 80° C., causing the gum to solidify. The resulting dark-brown solid was then collected by filtration, washed with water, methylene chloride and ether, and then dried under vacuum at 100° C., $10^{-3}$ torr to yield 9.0 g of brown cesium salt, containing about 96% by weight $Cs^+ C(SO_2CF_3)_2(SO_2C_2F_4N(CF_3)_2)$ according to NMR spectroscopic analysis.

Approximately 8 g of the cesium salt and 40 mL concentrated sulfuric acid were then charged to a short path distillation apparatus equipped with a dry ice condenser. Distillation was carried out at 63° C., $10^{-3}$ torr and the solid condensate collected by washing with ether. The ether solution was evaporated at 50° C., 20 torr to give an oily residue which was dissolved in 100 mL of water and treated with an aqueous solution of 20 g $Cs_2CO_3$. Gas ($CO_2$) was evolved and a white solid precipitated which was collected by filtration, washed with water and dried at 70° C. at ambient pressure to give 7.41 g of purified cesium salt.

The purified cesium salt was combined with 21.6 g LiCl, 75 mL water and 50 mL ether, and agitated vigorously for 1 hour to promote cation exchange. The ether phase was separated and the aqueous layer was then extracted with two additional 50 mL portions of ether. The combined ether extracts were, in turn, extracted with a fresh solution of 20 g LiCl in 75 mL water, followed by two 100 mL portions of deionized water. The ether phase was then isolated and evaporated to dryness at 40° C., 20 torr to give a viscous, light straw-colored oil.

The oil was dissolved in 250 mL water and filtered to remove particulates. Next, the filtrate was distilled to about half its original volume and the concentrate filtered again. The filtrate was then combined with 251 g toluene and the resulting mixture distilled using a Dean-Stark Trap to remove water, thereby causing the salt to precipitate as an oil from the remaining toluene. The salt gradually solidified upon cooling to room temperature, and was collected by filtration, washed with heptane and dried at 130° C., $10^{-3}$ torr to yield 4.88 g of a light straw-colored solid. NMR spectroscopy showed that this material contained 99.1% by weight of the title salt.

Example 5

Preparation of Dilithio
perfluoro(methyl-bis-sulfoethyl)amine
$CF_3N(CF_2CF_2SO_3^{31})_2 2Li^+$ (formula (7))

To a 500 mL flask fitted with an addition funnel, stir bar and reflux condenser was charged 11.4 g of $CF_3N(CF_2CF_2SO_2F)_2$ (prepared by electrochemical fluorination of methylamino bis-ethyl sulfonyl fluoride which, in turn, was prepared by double addition of methyl amine to vinylsulfonyl fluoride as described in Krutak et al., *J. Org. Chem.*, 44(2):3847–58 (1979)) and 200 mL of isopropanol. To the resulting two-phase mixture was added 180 mL of aqueous 1M LiOH in two aliquots. The resulting mixture was then stirred at room temperature overnight, after which it was evaporated to dryness under reduced pressure. The remaining white solid was washed with 500 mL of diethyl ether, followed by 300 mL of THF. The combined extracts were then evaporated under reduced pressure to yield 11.5 g of a white solid corresponding to the title compound. The structure was confirmed by $^1H$ and $^{19}F$ NMR.

Example 6

Preparation of Dilithio
perfluoro(methyl-bis-trifluoromethylsulfonimidoethyl)
amine $CF_3N(CF_2CF_2SO_2N^-SO_2CF_3)_2•2Li^+$
(formula (8))

A 500 mL flask equipped with an addition funnel and stir bar was charged with 10 g of $CF_3SO_2NH_2$, 45 mL of dry THF and 45 mL of dry triethylamine, then cooled to 0° C. under nitrogen. 15 g of $CF_3N(CF_2CF_2SO_2F)_2$ was then added slowly to the stirred solution. After complete addition, the reaction was allowed to warm to room temperature and stirred for an additional 92 hours. Next, the mixture was evaporated to a brown oil under reduced pressure, which was then dissolved in 300 mL of aqueous 1M LiOH. The water and other volatile components were then evaporated under reduced pressure and the remaining solid washed with 100 mL of diethyl ether. The ether solution was filtered, then evaporated under reduced pressure to yield a brown oil, which was dissolved in a small amount of ether, then added to 100 mL of methylene chloride. This solution was again filtered and evaporated to yield 3.5 g of a yellow solid corresponding to the title salt. The structure was confirmed by $^1H$ and $^{19}F$ NMR.

Example 7

Preparation of Lithium
bis-perfluoro(dimethylaminoethyl)sulfonimide
$Li^+ ^-N(SO_2C_2F_4N(CF_3)_2)_2$ (formula (9))

A 500 mL Fisher-Porter pressure bottle, equipped with a magnetic stir bar and pressure head, was charged with 30 g of $(CF_3)_2NC_2F_4SO_2NH_2$ (prepared by treatment of $(CF_3)_2NC_2F_4SO_2F$ with excess ammonia in tetrahydrofuran), 27.4 g of triethylamine and 31.8 g of $(CF_3)_2NC_2F_4SO_2F$. The flask was sealed and heated to 100° C. for 37 hrs with stirring. After cooling, the volatile components of the reaction mixture were evaporated under reduced pressure. The residue was dissolved in 300 mL of methylene chloride and extracted three times with 300 mL of water each time. The methylene chloride solution was then dried over $MgSO_4$, filtered, and the solvent removed under reduced pressure. The residue was then distilled from excess polyphosphoric acid over a temperature and pressure range starting from 105° C. and 3 torr and ending at 97° C. and 0.2 torr to yield 40.13 g of a pale yellow-orange liquid which solidified on standing. This solid, corresponding to $HN(SO_2C_2F_4N(CF_3)_2)_2$, was dissolved in 300 mL of methyl t-butyl ether, after which 20.6 g of $Li_2CO_3$ was added portion-wise with stirring. After stirring overnight, a small amount of additional $Li_2CO_3$ was added and heated briefly until the solution tested neutral to pH paper premoistened with distilled water. The mixture was cooled, filtered and the solvent removed under reduced pressure. Further drying under vacuum at 110° C. yielded 33.5 g of a fine white powder corresponding to the title salt. The structure of the product was confirmed by FTIR, and $^{19}$F and $^{1}$H NMR.

Example 8

Synthesis of Lithium Perfluoro(dimethylaminoethyl)sulfonate $(CF_3)_2NCF_2CF_2SO_3Li$ (formula (10))

The title compound was prepared by adding 41.5 g (0.12 mole) of $(CF_3)_2NC_2F_4SO_2F$ (prepared as described in Example 3) dropwise to a slurry of 10.1 g of $LiOH(H_2O)$ in 30 mL of water at 90° C. After addition was complete, the mixture was stirred for an additional 45 min., filtered through a 0.2 micrometer Gelman filter, and dried to a solid at 140° C. The resulting solid was then dissolved in diethyl ether, filtered, and the solvent removed under reduced pressure at 120° C. to yield the title compound. The structure of the compound was confirmed by $^{19}$F and $^{1}$H NMR. Cyclic voltammetry indicated stability from 0.5 to >4.5 volts, similar to commercial lithium salts. Specific conductivity of the sulfonate compound dissolved in 1/1 v/v mixture of propylene carbonate and dimethoxyethane at room temperature showed a peak conductivity of 5.3 mS/cm at a concentration of 0.6 moles/liter. This corresponds to the conductivity of lithium triflate at these conditions.

The inventive electrolyte compositions are particularly useful in that they control or prevent aluminum corrosion in electrochemical cells operating at voltages up to and including 5 V, referenced to lithium metal.

One way to assess the extent of aluminum corrosion is to measure the anodic current density vs. time response at a fixed d.c. potential of a cell containing a cathode having a freshly exposed aluminum surface, as described in the Examples section, below. The higher the current density, the more aluminum corrosion that is occurring.

Another way of assessing the extent of aluminum corrosion is to examine the a.c. impedance response of an aluminum cathode in the high frequency region (e.g., 100,000 to 100 Hz) before and after d.c. polarization, and to record the complex capacitance values, as described in the Examples section, below. An increase in the capacitance value following polarization indicates that corrosion of the base aluminum metal is occurring.

Test Methods

Corrosion current and complex capacitance measurements were made according to the technique generally described in Bard and Faulkner, *Electrochemical Methods: Fundamentals and Applications*, John Wiley and Sons, New York, 1980, pp. 350–53. An electrochemical cell was constructed having an aluminum working electrode, a lithium wire inserted in a luggin capillary (i.e., a glass capillary into which the electrode was inserted so that only the circular planar electrode surface was in contact with the electrolyte) as a reference electrode, and a 10 cm$^2$ platinum flag as an auxiliary electrode. The working electrode was fabricated from a 99.999% aluminum rod inserted into a Teflon sleeve to provide a planar electrode area of 0.07 cm$^2$. The native oxide layer was removed by first polishing the planar working surface with 3 mm aluminum oxide paper using hexane as a lubricant under ambient conditions, followed by a second polishing under an argon atmosphere.

After polishing, the cell was assembled under argon, connecting the three electrodes to a potentiostat which in turn was connected to a potential source. The cell was filled with approximately 10 mL of a 1M solution of the electrolyte salt dissolved in propylene carbonate. The solvent had been previously dried by stirring over $CaH_2$ for 24 hrs., followed by vacuum distillation. The final water content of the solvent was less than 50 ppm as measured by Karl Fischer titration. The electrolyte salt had been previously dried under vacuum at 120° C. for at least 18 hrs to a water content of less than 100 ppm, again determined by Karl Fischer titration. The impedance spectrum was collected at 5 mV, between the frequencies of 100,000 Hz and 0.1 Hz, and plotted in the complex plane as a function of the real and imaginary components of the electrode capacitance. The electrode was then polarized at +4.2 V vs Li (iR compensated) while the current was recorded vs. time. After 1 hr. the potential was removed and the cell allowed to reach open circuit potential over a period of 15 minutes. Once open circuit potential was reached, an a.c. impedance measurement was run as before with the data again plotted in the complex plane.

Current measurements (in microamps/cm$^2$), taken after 500 seconds and after 1000 seconds, are summarized in Table I, below. Data for the following salts is included for comparative purposes: $Li^+N(SO_2CF_3)_2$, $Li^+SO_3CF_3$, $Li^+PF_6$, and $Li^+Cl_4$ (designated COMP1, COMP2, COMP3, and COMP4, respectively in Table I).

TABLE I

| EXAMPLE | 500 s | 1000 s |
| --- | --- | --- |
| 1 | 2.5 | 1.5 |
| 3 | 560 | 530 |
| 4 | 3300 | 3171 |
| 5 | 9.1 | 6.6 |
| 7 | 3.4 | 2.1 |
| 8 | 21.7 | 21.3 |
| COMP1 | 25,500 | 26,250 |
| COMP2 | 103,142 | 74,285 |
| COMP3 | 8.7 | 6.3 |
| COMP4 | 55 | 46 |

Complex capacitance data (in microfarads/cm$^2$) before and after d.c. polarization is presented in Table II. Data for $Li^+N(SO_2CF_3)_2$ and $Li+PF_6$ (designated COMP1 and COMP3, respectively, in Table II) is included for comparative purposes.

TABLE II

| EXAMPLE | Capacitance Before | Capacitance After |
| --- | --- | --- |
| 1 | 8 | 2.2 |
| 7 | 4.1 | 3.0 |
| COMP1 | 14 | 1,030 |
| COMP3 | 14 | 3.3 |

As shown in Tables I and II, electrolyte compositions according to the invention are less corrosive than known electrolyte compositions containing other perfluoro-organo-sulfonyl salts. In some instances, electrolyte compositions according to the invention approach or exceed the performance of inorganic salts such as $Li^+PF_6$ and $Li^+ClO_4$ which are known not to promote corrosion. The inventive electrolyte salts are uniquely capable of inhibiting aluminum corrosion at high electrochemical potentials (potentials greater than +3.5 volts vs. Li/Li$^+$); while, at the same time providing very good ionic conductivity and stability (e.g. thermal, electrochemical, and hydrolytic stability).

The utility of the electrolyte composition of formula 10 has been investigated in a polymer matrix (polyethylene oxide having a molecular weight of about 900,000). The composition was found to have an ion transport number of t+=0.45. In contrast, Li$^+$N$^-$(SO$_2$CF$_3$)$_2$ exhibited an ion transport number of only t+=0.25.

What is claimed is:

1. An electrolyte composition comprising a salt disposed in a matrix, said salt having a formula selected from the group consisting of

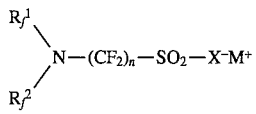

and

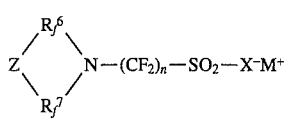

in which X$^-$ is selected from the group consisting of —O$^-$, —N$^-$SO$_2$R$_f^3$ and

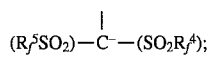

Z is selected from the group consisting of —CF$_2$—, —O—, —NR$_f^8$—, and —SF$_4$—; R$_f^1$ and R$_f^2$, independently, are selected from the group consisting of —CF$_3$, —C$_m$F$_{2m+1}$, and —(CF$_2$)$_q$—SO$_2$—X$^-$M$^+$; R$_f^3$, R$_f^4$, and R$_f^5$, independently, are selected from the group consisting of —CF$_3$, —C$_m$F$_{2m+1}$, —(CF$_2$)$_q$—SO$_2$—X$^-$M$^+$,

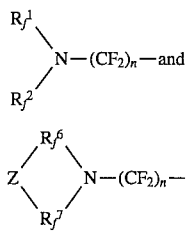

R$_f^8$ is selected from the group consisting of —CF$_3$, —C$_m$F$_{2m+1}$, and —(CF$_2$)$_q$—SO$_2$—X$^-$M$^+$; R$_f^6$ and R$_f^7$, independently, are perfluoroalkylene moieties having the formula —C$_r$F$_{2r}$; where n is 1–4; r is 1–4; m is 1–12; q is 1–4; and M$^+$ is a counterion.

2. The electrolyte composition of claim 1 wherein M$^+$ is selected from the group consisting of alkali metals, alkaline earth metals, transition metals, rare earths, NH$_{(4-j)}$R$_j^+$, R$_j$C(NH$_{(2-j)}$R$_j$)$_2^+$, and C(NH$_{(2-j)}$R$_j$)$_3$ in which j is 0–2 and R$_j$ is selected from the group consisting of —H, an alkyl group, an oxalkyl group, or an aryl group.

3. The electrolyte composition of claim 1 wherein M$^+$ is a lithium ion.

4. The electrolyte composition of claim 1 wherein said salt is selected from the group consisting of those having the following formulas:

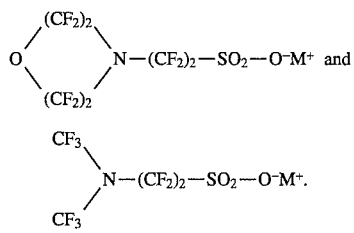

5. The electrolyte composition of claim 1 wherein said salt is selected from the group consisting of those having the following formulae:

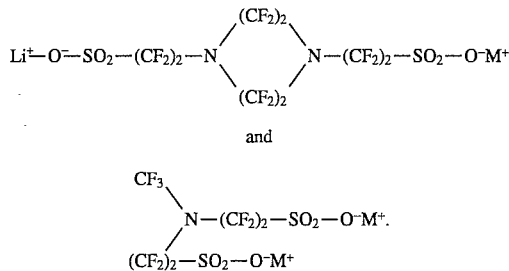

6. The electrolyte composition of claim 1 wherein said salt has the formula

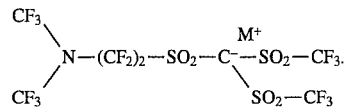

7. The electrolyte composition of claim 1 wherein said salt is selected from the group consisting of those having the following formulae:

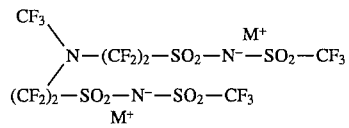

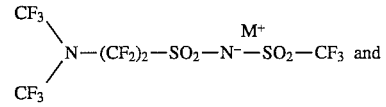

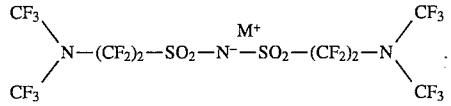

8. The electrolyte composition of claim 1 further comprising a salt selected from the group consisting of M$^+$BF$_4^-$; M$^+$SbF$_6^-$; M$^+$AsF$_6^-$; M$^+$ClO$_4^-$; M$^+$C$^-$(SO$_2$CF$_3$)$_3$; M$^+$PF$_6^-$; CF$_3$SO$_3^-$M$^+$; (CF$_3$SO$_2$)$_2$N$^-$M$^+$; and combinations thereof, where M$^+$ is a counterion.

9. The electrolyte composition of claim 1 wherein said matrix comprises a matrix selected from the group consisting of polymers, aprotic liquids, and mixtures thereof.

10. The electrolyte composition of claim 1 wherein said matrix comprises an aprotic liquid medium.

11. A battery comprising:

at least one positive electrode;

at least one negative electrode; and an electrolyte comprising a salt disposed in a matrix, said salt having the formula selected from the group consisting of

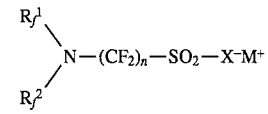

and

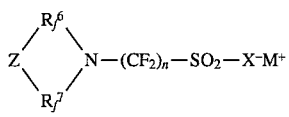

in which $X^-$ is selected from the group consisting of $O^-$, $N^-SO_2R_f^3$, and

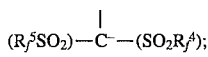

Z is selected from the group consisting of $-CF_2-$, $-O-$, $-NR_f^8-$, and $-SF_4-$; $R_f^1$ and $R_f^2$, independently, are selected from the group consisting of $-CF_3$, $-C_mF_{2m+1}$, and $-(CF_2)_q-SO_2-X^-M^+$, $R_f^3$, $R_f^4$, and $R_f^5$, independently, are selected from the group consisting of $-CF_3$, $-C_mF_{2m+1}$, $-(CF_2)_q-SO_2-X^-M^+$,

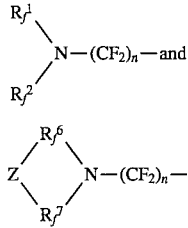

$R_f^8$ is selected from the group consisting of $-CF_3$, $-C_mF_{2m+1}$, and $-(CF_2)_q-SO_2-X^-M^+$; $R_f^6$ and $R_f^7$, independently, are perfluoroalkylene moieties having the formula $-C_rF_{2r}-$; where n is 1–4; r is 1–4; m is 1–12; q is 1–4; and $M^+$ is a counterion.

12. The battery of claim 11 wherein said negative or positive electrode comprises an aluminum current collector.

13. A salt having a formula selected from the group consisting of

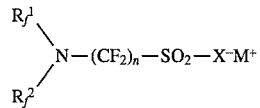

and

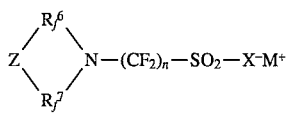

in which $X^-$ is selected from the group consisting of $-N^-SO_2R_f^3$ and

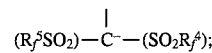

Z is selected from the group consisting of $-CF_2-$, $-O-$, $-NR_f^8-$, and $-SF_4-$; $R_f^1$ and $R_f^2$, independently, are selected from the group consisting of $-CF_3$, $-C_mF_{2m+1}$, and $-(CF_2)_q-SO_2-Q^-M^+$; Q is selected from the group consisting of $-O^-$, $-N^-SO_2R_f^3$ and

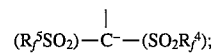

$R_f^3$, $R_f^4$, and $R_f^5$, independently, are selected from the group consisting of $-CF_3$, $-C_mF_{2m+1}$, $-(CF_2)_q-SO_2-Q^-M^+$,

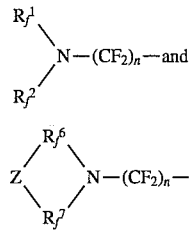

$R_f^8$ is selected from the group consisting of $-CF_3$, $-C_mF_{2m+1}$, and $-(CF_2)_q-SO_2-Q^-M^+$; $R_f^6$ and $R_f^7$, independently, are perfluoroalkylene moieties having the formula $-C_rF_{2r}-$; where n is 1–4; r is 1–4; m is 1–12; q is 1–4; and $M^+$ is a counterion.

14. The salt of claim 13 which is selected from the group consisting of those having the following formulae:

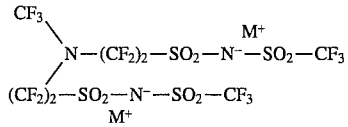

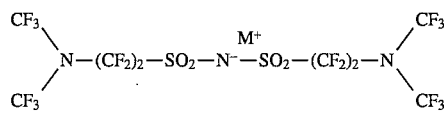

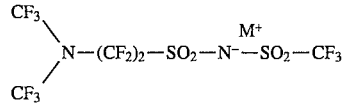

and

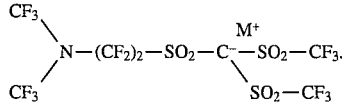

* * * * *

UNITED STATES PATENT AND TRADEMARK OFFICE
CERTIFICATE OF CORRECTION

PATENT NO. : 5,514,493
DATED : May 7, 1996
INVENTOR(S) : Jennifer Waddell et al.

It is certified that error appears in the above-indentified patent and that said Letters Patent is hereby corrected as shown below:

Column 1, line 56

"$Zn^+$" should be -- $Zn^{++}$ --

Column 2, line 24

"$R_f^2$" should be -- $R_f^7$ --

Column 8, line 49

"$^{16}F$" should be -- $^{19}F$ --

Column 12, line 26

"$Li^{+-}Cl_4$" should be -- $Li^{+-}ClO_4$ --

Signed and Sealed this

Second Day of September, 1997

Attest:

*Attesting Officer*

BRUCE LEHMAN
Commissioner of Patents and Trademarks